United States Patent
Lannoy

(10) Patent No.: US 8,246,566 B2
(45) Date of Patent: Aug. 21, 2012

(54) TOTAL FLUID LOSS CONTROL SYSTEM

(75) Inventor: Jean-Michel Lannoy, Anstaing (FR)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 508 days.

(21) Appl. No.: 11/960,529

(22) Filed: Dec. 19, 2007

(65) Prior Publication Data

US 2008/0154170 A1 Jun. 26, 2008

Related U.S. Application Data

(60) Provisional application No. 60/876,769, filed on Dec. 22, 2006.

(51) Int. Cl.
*A61M 37/00* (2006.01)
*C02F 1/44* (2006.01)

(52) U.S. Cl. ............... 604/5.04; 604/4.01; 604/6.09; 604/6.11; 210/645; 210/646; 210/739

(58) Field of Classification Search ............ 604/4.01, 604/5.01, 5.04, 6.09, 6.11, 6.16, 65–67; 210/739, 210/645, 646
See application file for complete search history.

(56) References Cited

U.S. PATENT DOCUMENTS

| | | | |
|---|---|---|---|
| 4,204,957 A | 5/1980 | Weickhardt | |
| 4,728,433 A | 3/1988 | Buck et al. | |
| 5,211,849 A * | 5/1993 | Kitaevich et al. | 604/5.04 |
| 2002/0032403 A1* | 3/2002 | Savagle et al. | 604/28 |
| 2005/0045540 A1 | 3/2005 | Connell et al. | |
| 2006/0226079 A1 | 10/2006 | Mori et al. | |

OTHER PUBLICATIONS

International Search Report PCT/US2007/088541/ International Filing Date Dec. 21, 2007.
European Office Action for Application No. 07 855 318.7-2310 dated Oct. 17, 2011.

* cited by examiner

*Primary Examiner* — Leslie Deak
(74) *Attorney, Agent, or Firm* — K&L Gates LLP

(57) ABSTRACT

A system or method controls total fluid loss (TFL) in a patient undergoing hemofiltration therapy administered through an extracorporeal circuit by frequently calculating and storing a retrievable value representing TFL. At session start or restart, the value is read to determine whether TFL is out of tolerance, and if so, fluid balance is restored before administering a prescribed therapy. The TFL value is calculated during therapy by measuring fluid added to the circuit and fluid removed from the circuit, and the result is stored as an updated value. If TFL drifts out of tolerance fluid flow rates may be temporarily changed until a desired fluid balance is restored. The system may include a microprocessor based advanced controller receiving the fluid measurements as feedback for regulating substitution fluid and filtrate flow rates, and updating the TFL, value in non-volatile memory.

16 Claims, 8 Drawing Sheets

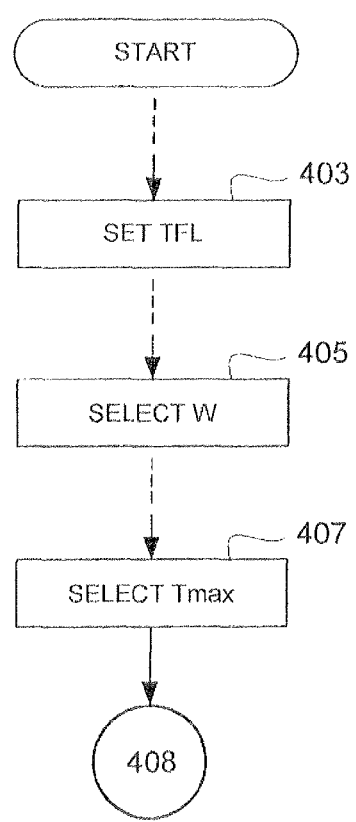
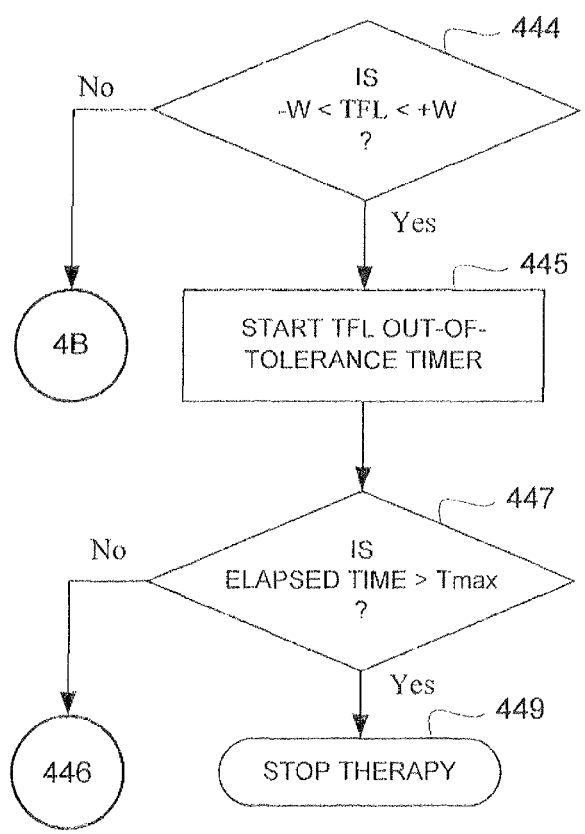
FIG. 5
FIG. 6

TOTAL FLUID LOSS CONTROL SYSTEM

CLAIM OF PRIORITY UNDER 35 U.S.C. §119

The present Application for Patent claims priority to U.S. Provisional Application No. 60/876,769 entitled "TOTAL FLUID LOSS CONTROL SYSTEM," filed Dec. 22, 2006, and assigned to the assignee hereof and hereby expressly incorporated by reference herein.

BACKGROUND

1. Field

The invention relates generally to blood filtration and to continuous renal replacement therapy (CRRT). More specifically, the invention relates to monitoring fluid loss and fluid replacement during CRRT therapy and automatically controlling fluid flow rates to achieve a desired balance.

2. Background

Extracorporeal blood treatment therapy is widely used for critically ill patients. Many of these patients suffer from acute renal failure and are treated in an Intensive Care Unit (ICU) with various forms of hemofiltration, known generally as Continuous Renal-Replacement Therapy (CRRT). Many different CRRT techniques are used today, including Continuous Veno-Venous Hemofiltration (CVVH), Continuous Arterio-Venous Hemofiltration (CAVH), and Continuous Veno-Arterial Hemofiltration (CVAH). In hemofiltration, blood from a patient is directed into an extracorporeal circuit and made to flow under pressure through a blood filter, or hemofilter. The hemofilter contains a semi-permeable membrane that separates water and waste solutes from the main flow of blood. The filtered blood is then returned to the patient.

Another form of renal replacement therapy that can be used for patients with renal failure in Intensive Care Units (ICUs) is hemodialysis. Hemodialysis differs from hemofiltration in that a specially formulated dialysate fluid is made to flow along a side of the semi-permeable membrane opposite to the side where blood flows. Concentration gradients across the membrane encourage the migration of unwanted solutes away from the blood into the dialysate by osmosis.

Hemodialysis usually can only be applied for a few hours per day, and as such, is more restrictive and sometimes less effective than pure hemofiltration. However, hemodialysis can be combined with hemofiltration to provide more complex blood filtration therapies. Examples of such combined techniques are Continuous Veno-Venous Hemodiafiltration (usually abbreviated as CVVHD or CVVHDF) and Continuous Arterio-Venous Hemodiafiltration (usually abbreviated as CAVHD or CAVHDF).

Typically, a hemofilter, or artificial kidney is used during CRRT therapy. The artificial kidney may be formed of hollow-fibers or closely separated plates, and is connected to a patient's bloodstream through an extracorporeal circuit. In CVVHD, the supply from and return to the blood of the patient is made via two venous accesses, using a blood pump to provide the driving force for the transport of blood from the patient into the artificial kidney and back to the patient. In CAVHD, the access which provides the supply of blood to the artificial kidney is made through an artery, and the return of the blood to the patient is made through a vein. Thus, blood pumps are not generally used in CAVHD because the arterial blood pressure provides the driving force to transport the blood. Because a pump provides better control of blood flow, and because CVVHD avoids arterial catheter-related complications, CVVHD is a preferred renal replacement therapy in ICUs over CAVHD.

In CVVHD, the patient's blood is passed through the artificial kidney over a semipermeable membrane. The semipermeable membrane selectively allows plasma water and matter in the blood to cross the membrane from the blood compartment into the filtrate compartment, mimicking the natural filtering function of a kidney. This leads to a considerable loss of fluid from the blood, which is removed as the filtrate in the artificial kidney. Every liter of filtrate fluid that is removed in the artificial kidney contains a large fraction of the molecules that are dissolved in the plasma, such as urea, creatinine, phosphate, potassium, sodium, glucose, amino acids, water-soluble vitamins, magnesium, calcium, sodium, and other ions and trace elements. The fraction of molecules that pass the semipermeable membrane depends on the chemical characteristics of the molecules, the structure of the membrane, and the transmembrane pressure (TMP). In order to keep the blood volume of the patient constant, a substitution fluid may be added to the bloodstream in the extracorporeal circuit downstream of the artificial kidney and upstream of the venous return catheter.

In a normal CVVHD procedure, approximately 50 liters of filtrate are removed per 24 hours, and approximately the same amount of substitution fluid is added to the bloodstream. The substitution fluid commonly used is conventional infusion fluid comprising a physiological saline solution generally containing about 140 mmol/L of sodium ions, 1.6 mmol/L of calcium ions, 0.75 mmol/L of magnesium ions, 36 mmol/L of bicarbonate ions, and 110 mmol/L of chloride ions.

In modern ICU settings, performing any type of CRRT requires the use of a CRRT machine for controlling blood flow through an extracorporeal circuit. Typically, a CRRT machine draws blood from a patient through an access line using a blood pump (e.g., a peristaltic pump), and returns the blood to the patient through a return line. The flow rate of the blood pump, the design of the artificial kidney, and the type of CRRT therapy used, determines the fluid loss rate from the bloodstream through the filter.

Pressure sensors throughout the extracorporeal circuit may be used to sense and alarm fluid flow at various points. For example, an access line pressure sensor may sense pressure of blood entering the extracorporeal circuit, and generate an alarm in the event the sensor senses an out-or-range condition. Similarly, a return line pressure sensor may also sense and transmit pressure signals and generate alarms. Pressure sensors placed before the hemofilter, in the filtrate outflow, and in the return line provide measurements needed to calculate TMP or the pressure drop (PD) in blood flowing through the artificial kidney. CRRT machines may also include other protective features such as air bubble traps, air bubble detectors, and automatic clamps to prevent air bubble migration through the return line and back to the patient. Anticoagulation additives such as heparin or citrates may also be added to the circuit using more complex processes.

In a technique known as Slow Continuous Ultra-Filtration (SCUF) therapy, a filtration pump can be used to remove plasma water (ultrafiltrate or UF) from the blood circulating into the artificial kidney. The UF is typically collected inside a filtration container and continuously weighed by a filtration scale. In CVVH therapy, a filtration pump may be used to remove UF from the blood circulating into the artificial kidney and to direct the UF to a filtration container. In both of these therapies, a substitution fluid or replacement fluid is typically injected into the circulating blood to make up for fluid loss through the artificial kidney. The substitution fluid may be added as a pre-dilution supplement or a post-dilution supplement. When added as a pre-dilution supplement, the substitution fluid is injected upstream of the hemofilter. When added as a post-dilution supplement, the substitution fluid is injected downstream of the hemofilter. In both cases, injection of the substitution fluid may be effected by a separate substitution pump. Some CRRT machines allow both pre-dilution and post-dilution together and therefore are configured with two substitution pumps. The source of substitution fluid is typically a container suspended near the CRRT machine. Some CRRT machines are configured to use one scale for weighing pre-dilution substitution fluid and another scale for weighing post-dilution substitution fluid.

During CVVHD therapy, dialysate fluid flows into the dialysate compartment of the artificial kidney, and a filtration pump is used to remove used dialysate (or effluent) from the blood circulating through the artificial kidney. The effluent is collected inside a filtration container and may also be weighed to monitor fluid loss.

In CVVHDF therapy, a filtration pump is used to remove UF from the blood circulating through the artificial kidney. The UF may also be collected in a filtration container and weighed. Substitution fluid (pre-dilution or post-dilution) and dialysate may also be provided and periodically weighed. CRRT machines have been configured using a separate scale for weighing dialysate fluid, and using a separate or common scale for weighing pre-dilution and post-dilution fluids.

All of the above therapies may include a procedural safeguard where UF or plasma fluid lost through the artificial kidney can be compared to the amount of substitution fluid added to the extracorporeal circuit. The difference yielded by this comparison is the total fluid loss (or gain) TFL. In most therapies, TFL is ideally maintained at zero, i.e., no net loss of vital fluids.

There are two common techniques for detecting TFL in CRRT machines: direct regulation and differential regulation.

Direct regulation calculates TFL by reading weight values for both filtration fluid and substitution fluid at regular time intervals. The weighed value of filtration fluid is compared to an expected value of filtration fluid calculated by the CRRT machine. Any difference between weighed and expected values yields a correction signal that adjusts filtration flow rate caused by the filtration pump. Similarly, the weighed value of substitution fluid is compared to an expected value of substitution fluid calculated by the CRRT machine. Any difference between weighed and expected values yields a correction signal that adjusts substitution flow rate caused by the substitution pump. In this manner, the performance of each pump is individually controlled to meet predetermined performance criteria.

Differential regulation calculates TFL by continuously measuring weight change of filtration and substitution fluids over the same time period. The change in filtration fluid in a single period is subtracted from the change in substitution fluid over the same time period, yielding a value for TFL. This value is compared to a predetermined value of expected TFL. If the comparison yields a difference, a correction signal is generated to balance the system, i.e., to govern one or both of the filtration and substitution pump flow rates and cause TFL to converge toward zero or some other desired value.

Both direct and differential regulation schemes have limitations. When regulation cannot achieve a desired balance, an alarm may be generated. The alarm setpoint is typically fixed by the manufacturer of the CRRT machine. Often the alarm setpoint is fixed at around 50 g when treating adult patients, and at around 20 g when treating pediatric patients. This alarm is commonly known as a "balance alarm".

When a balance alarm occurs, the treatment pumps (substitution, dialysate and/or filtration pumps) stop. In such a case, the system will remain inoperative until the user (e.g., a health care professional) identifies the cause of the alarm, rectifies the problem, and restarts the CRRT machine. However, restarting the CRRT machine reinitializes the system without recognizing that the patient has experienced a fluid imbalance equivalent to the balance alarm setpoint. In other words, the CRRT machine (treating an adult patient) will restart without accounting for a pre-existing plus-or-minus 50 g fluid imbalance, and unfortunately attempt to maintain that same imbalance throughout the therapy.

If the user fails to solve the underlying problem that drives the system into an unbalanced condition before restarting the system, serious hemodynamic instability can result. When the CRRT machine is restarted, a second balance alarm may occur a short time later. Then, after a subsequent restart, an additional error equal to the setpoint value will be added to the first error. As errors accumulate in this manner, fluid level in a patient can become dangerously imbalanced while the CRRT machine indicates normal operating conditions. For example, restarting 10 times without resolving the underlying control problem could generate a 500 g increase or decrease in fluid level. In an ICU setting, such hemodynamic instability could be fatal.

SUMMARY

One specific embodiment or the invention relates to systems or methods for avoiding excessive fluid overload or excessive fluid loss generated by uncontrolled balance alarms during continuous or intermittent blood filtration therapy administered through CRRT or dialysis machines. Uncontrolled balance alarms are encountered in machines having a differential or direct scale regulation system and, therefore, these machines are examples of machines where this embodiment can be used.

Another embodiment of the invention provides systems or methods to control total fluid loss (TFL) in a patient over the course of hemofiltration therapy administered through an extracorporeal circuit, whether the therapy occurs in one session or over several sessions. TFL is frequently calculated by measuring the total amount of fluids added to the circuit and the total amount of fluids removed from the circuit, computing their difference, and storing the result in retrievable memory as an updated value. At session start or restart, this stored value is read to determine whether TFL is out of tolerance, and if so, fluid balance is restored before administering a prescribed therapy. During therapy, if TFL drifts out of tolerance, fluid flow rates may be temporarily changed until a desired fluid balance is restored.

The above systems may include a microprocessor based advanced control system that receives fluid measurements as feedback for regulating substitution fluid and filtrate flow rates, and updating the TFL value in nonvolatile memory. The advanced control system may determine a filtrate flow rate based on inputs received through a user interface, including a specified input for substitution fluid flow rate, and a prescribed input representing a fluid loss rate. The microprocessor may output control signals representing a filtrate flow rate and a substitution fluid flow rate, respectively, to filtrate and substitution fluid pumps in the extracorporeal circuit.

In one embodiment, the invention provides a hemofiltration system for administering a hemofiltration therapy to a patient in such a way that even if the therapy is interrupted and restarted at least once, the system remembers the state of the patient's total fluid loss upon restart. The system can then continue the therapy without risk of driving the fluid state into an imbalanced condition. In this embodiment the system may include an extracorporeal circuit, a filtrate measurement instrument, a substitution fluid measurement instrument, a memory device for storing a value for total fluid loss, and a subsystem for updating the total fluid loss value stored in the memory device using input signals from transmitting instruments in the extracorporeal circuit. When therapy is restarted after an interruption, the stored value of total fluid loss may be used to control the fluid state of the patient. The extracorporeal circuit may include an access port for drawing blood from the patient, a blood pump in fluid communication with the access port, a hemofilter receiving blood from the blood pump, a filtrate pump drawing the filtrate flow from the hemofilter, a filtrate collector collecting filtrate flowing from the filtrate pump, a fluid container containing a volume of substitution fluid, a substitution fluid pump drawing substitution fluid from the fluid container and providing a flow of substitution fluid supplementing the filtered blood flow, and a return port receiving the supplemented filtered blood flow for return to the patient. The hemofilter may have a semi-permeable membrane separating water and waste solutes from the blood such that the separated water and waste solutes exit the hemofilter as filtrate flow, and the separated blood exits the hemofilter as filtered blood flow. The filtrate measurement instrument measures the weight of filtrate accumulated in the filtrate collector, and may be coupled to a first transmitting instrument for transmitting a signal correlated to the filtrate weight. The substitution fluid measurement instrument measures the weight of fluid remaining in the fluid container, and may be coupled to a second transmitting instrument for transmitting a signal correlated to the substitution fluid weight.

The method may include process steps for adding substitution fluid into the extracorporeal circuit at a desired substitution fluid flow rate, removing filtrate from the circuit at a desired filtrate flow rate, measuring the total amount of substitution fluid added to the circuit, measuring the total amount of filtrate removed from the circuit, calculating TFL based on total amounts measured in the measuring steps, and storing the calculated TFL value in retrievable memory. Additional method steps may include a step for determining if the TFL value is out of tolerance, and, if the value is out of tolerance high, removing filtrate from the circuit without adding substitution fluid until the desired TFL balance is attained, or if the value is out of tolerance low, adding substitution fluid to the circuit without removing filtrate until the desired TFL balance is attained. At therapy session start-up or restart, the method may further include a step for checking the stored TFL value for an out-of-tolerance condition, and if such condition is found, restoring the patient's TFL to the desired balance before resuming normal operation.

BRIEF DESCRIPTION OF THE DRAWINGS

The features, objects, and advantages of the invention will become more apparent from the detailed description set forth below when taken in conjunction with the drawings, wherein:

FIG. 5 is a partial flow chart illustrating optional initialization steps for a method according to an embodiment of the invention.

FIG. 6 is a flow chart illustrating a control algorithm for implementing a safety feature to limit duration of an out-of-tolerance fluid imbalance in a method according to an embodiment of the invention.

DETAILED DESCRIPTION

Throughout this disclosure, the term "total fluid loss" or TFL indicates a state of fluid balance within a patient, relative to an initial condition. Thus, TFL, may describe a net fluid gain or a net fluid loss. In case of a net fluid gain, TFL is positive. In case of a net fluid loss, TFL is negative.

The term "ultrafiltrate variation" (or $\Delta UF$) indicates the difference between a prescribed fluid loss rate and an actual fluid loss rate, where the actual fluid loss rate is based on physical measurements. Actual fluid loss rate may be determined as the difference between fluid loss from an extracorporeal circuit (e.g., filtrate collected from a hemofilter) minus fluid gain in the same circuit (e.g., substitution fluid added) over a selected time period T. For example, in CVVHD therapy, fluid loss may be measured by reading a filtration scale, and fluid gain may be measured by summing readings on a substitution fluid scale and on a dialysate scale. UF variation may then be calculated as the prescribed fluid loss during time period T, plus a filtration scale variation during time period T, minus the sum of substitution and dialysate scale variations during time period T.

Figure 1:
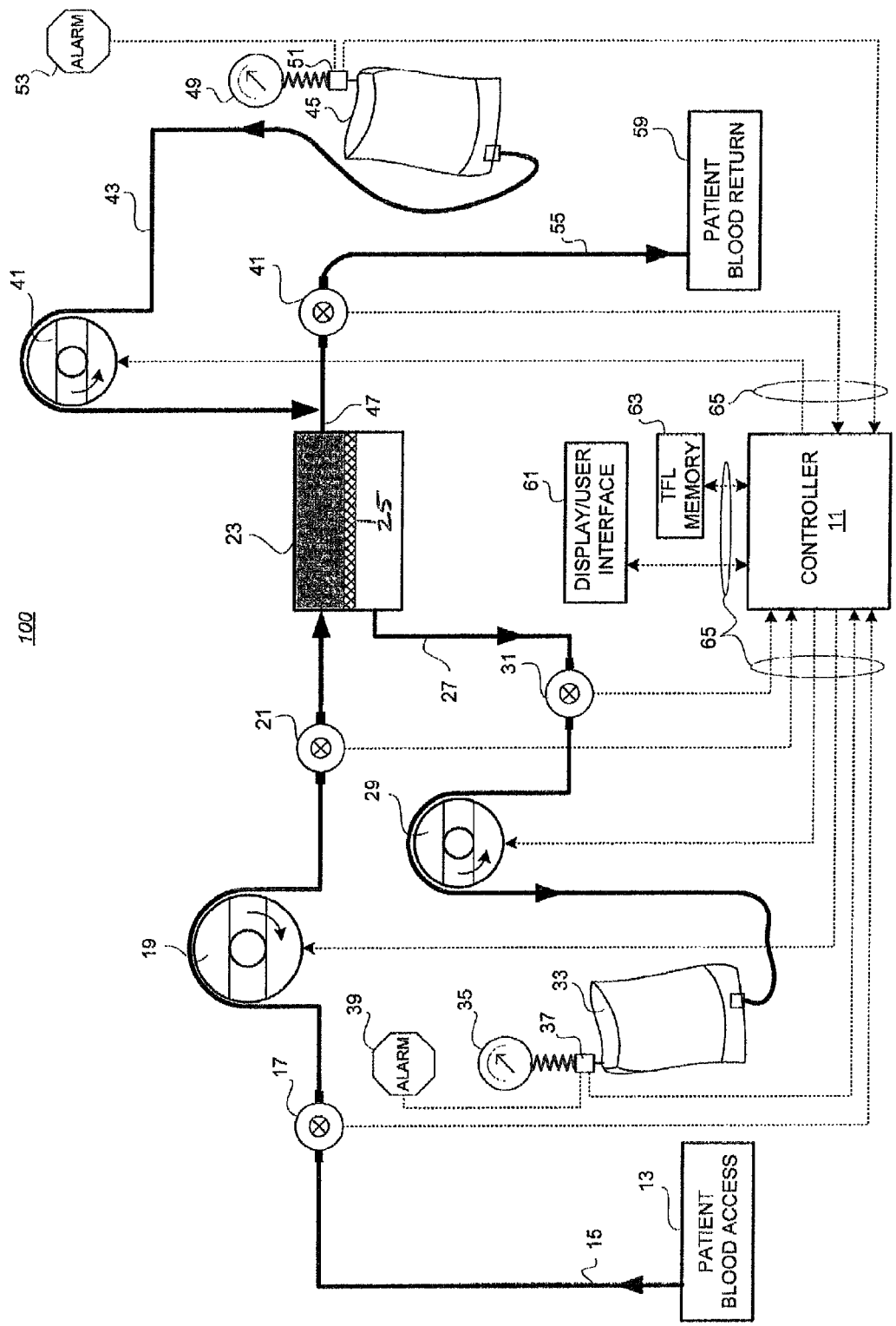
FIG. 1 is a schematic diagram of a system for controlling TFL in a patient undergoing hemofiltration therapy according to an embodiment of the invention.

FIG. 1 is a schematic diagram of a system 100 for controlling TFL in a patient undergoing hemofiltration therapy according to an embodiment of the invention. The system 100 includes a controller 11 that interfaces with components of an extracorporeal blood filtration circuit. The extracorporeal circuit begins at a patient access site 13, which may represent one or more intravenous (I-V) catheters, PICC lines or central venous catheters or equivalent means for penetrating a blood vessel of the patient to draw unfiltered blood into the circuit. The blood flows through an access line 15 to a sensor 17.

The sensor 17 may be a blood flow detector or blood pressure sensor and may be provided to measure the flow or pressure of blood leaving the patient at the access site 13. The sensor 17 may be any detector known in the art and commonly used for this purpose, such as a non-invasive infrared or ultrasonic Doppler type detector. In one embodiment, the sensor 17 may be a pressure sensor for detecting a differential pressure between two points in the blood flow, for derivation of a signal representative of the blood flow. The sensor 17 may transmit this signal to the controller 11 for purposes of feedback controls which is explained in further detail below.

Blood flow leaving the sensor 17 is drawn and pumped through a blood pump 19. The blood pump 19 provides a mechanical force for sustaining a continuous flow of blood through the circuit and it may be any conventional pump known in the medical arts and suitable for this purpose. Thus, the blood pump 19, as well as other pumps described herein or otherwise used in different embodiments of the invention, may be conventional diaphragm, centrifugal, or peristaltic pumps typically used in the medical arts. The flow rate delivered by the blood pump 19 may be regulated by the controller 11.

A pre-filter sensor 21 may be installed to measure pressure in blood flow 15 upstream of a hemofilter 23. The hemofilter 23 may be of conventional design and selected from commercial stock, and may include two or more flow paths separated from each other by a semipermeable membrane 25. The semipermeable membrane 25 may be selected for its particular pore size, i.e., its ability to pass molecules up to a certain atomic weight.

By osmotic or hydrostatic pressure, water and waste solutes in the blood flow 15 pass through the semi-permeable membrane 25 and exit the hemofilter 23 along a flow path as filtrate flow 27. A filtrate pump 29 may be installed to draw the filtrate flow 27 from the hemofilter 23. A sensor 31 may be located in the filtrate flow 27 to measure pressure in that line. The filtrate in flow 27 may be collected in a filtrate collector 33 and weighed by a filtrate scale 35. The filtrate scale 35 may include a transmitter 37 for transmitting a signal representing the accumulated weight of filtrate collected in the filtrate collector 33. The transmitter 37 may transmit the signal to the controller 11. A filtrate alarm 39 may be connected to the filtrate scale 35 to provide an alarm in case the filtrate collector 33 becomes filled to capacity.

In some embodiments, the extracorporeal circuit may be configured for hemodialysis or hemodiafiltration. In these embodiments, a dialysate pump (not shown) may force dialysate through the lower portion of the hemofilter 23 into the flow path 27.

Substitution fluid may be added to the blood flow 15, upstream of the hemofilter 23 as a pre-dilution substitution fluid or downstream of the hemofilter 23 as a post-dilution substitution fluid. The substitution fluid may be any suitable sterile intravenous fluid having a concentration of electrolytes similar to the patient's blood plasma. The system 100 shows an embodiment configured for post-dilution substitution fluid. The substitution fluid pump 41 may substitute fluid flow 43 from a fluid container 45 and add it to the blood flow 47 exiting the hemofilter 23. The flow rate of the substitution fluid delivered by the fluid pump 41 may be governed by the controller 11.

As the substitution fluid is drawn from the fluid container 45, the amount of substitution fluid delivered to the circuit may be measured using a substitution fluid scale 49. The scale 49 may be equipped with a transmitter 51 for transmitting a signal representing the amount to the controller 11. A substitution fluid alarm 53 may be connected to the substitution fluid scale 49 to provide an alarm in case the fluid container 45 becomes empty.

The blood flow 47 exiting the hemofilter 23 mixes with the substitution fluid flow 43 to form a return flow 55. A sensor 57 may be provided downstream of the combined fluids to measure flow or pressure and transmit a signal to the controller 11. The return flow may then re-enter the patient's corporeal bloodstream through another access site 59, for example, an installed venous catheter. Upstream of access site 59, additional safety features (not shown) may be added to the return line, such as air bubble traps, air bubble detectors, and automatic clamps.

The controller 11 may be a general purpose computer, personal computer, or other suitable microprocessor-based component or microcontroller known in the art. The controller 11 may receive various input signals and send various control signals over the signal lines 65 indicated by the dashed lines of FIG. 1. The signal lines 65 may be cable or wireless. The signal lines 65 may enable the controller 11 to receive feedback signals from sensors in the extracorporeal circuit to allow the controller 11 to regulate fluid flow rates such as blood flow rate, dialysate flow rate, filtrate flow rate and substitution fluid flow rate. In addition, the signal lines coupled between the controller 11 and the transmitters 37 and 51 may enable the controller 11 to monitor TFL during hemofiltration therapy. Using control algorithms, the controller 11 may adjust substitution fluid and filtrate flow rates as necessary to maintain a prescribed fluid loss rate (FLR).

A prescribed value for FLR may be input to the controller 11 via a user interface 61. The user interface 61 may be a keyboard or other conventional device used for inputting commands, writing code, or loading software. The user interface 61 may be combined with a display unit, such as a touchscreen display or a laptop computer. A memory 63 may be coupled to, or otherwise accessible by, the controller 11. In one embodiment, the memory 63 is called the TFL memory, which indicates that the memory functions to store a value representing TFL, calculated by the controller 11. For example, the controller 11 may receive input from the scales 35 and 49 over the signal lines 65 and execute an algorithm to calculate a value for TFL. Once the value for TFL, is calculated, the controller 11 may store the value in the memory 63. In another embodiment, the memory 63 may also store control algorithms executable by the controller 11 for controlling fluid flow rates. Preferably, the memory 63 is a non-volatile memory such as an EEPROM.

Figure 2:
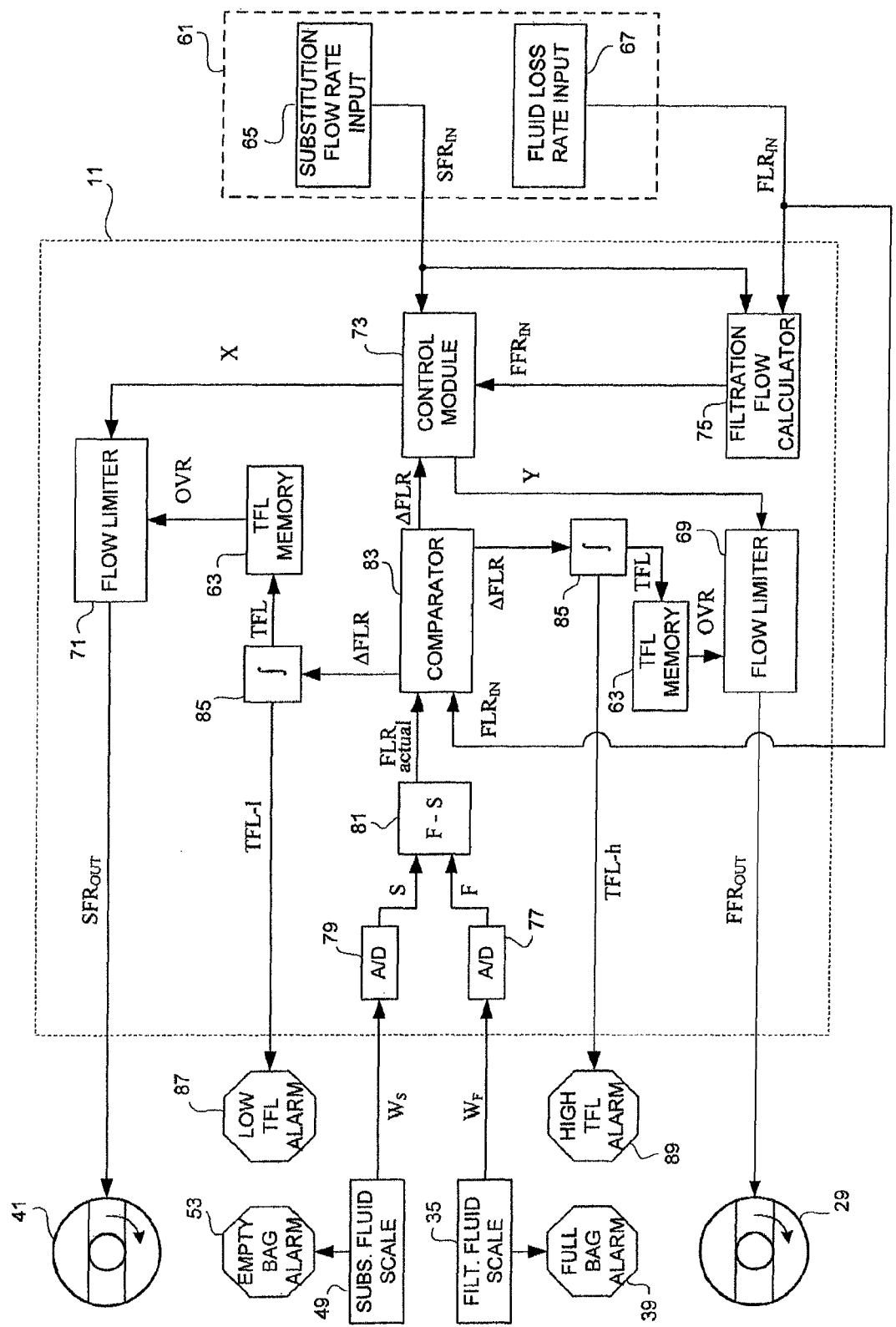
FIG. 2 is a block diagram of a control system according to an embodiment of the invention.

One embodiment of a control system is depicted in FIG. 2. This figure illustrates a system 200, which shows the controller 11 in greater detail. In this embodiment, the controller 11, which is represented by the large dashed block, may be a computer, microprocessor, or microcontroller having integral hardware modules, software modules, or a combination thereof. Using the various modules, the controller 11 may monitor and/or control TFL in a hemofiltration circuit by comparing actual fluid loss data to prescribed fluid loss data. If a difference exists, the controller 11 may correct the difference by adjusting the control signals that govern fluid flow in the circuit.

The controller 11 may have four inputs and four outputs. The four inputs are substitution fluid scale input Ws, filtrate scale input Wf, user-specified substitution flow rate input SFRin, and user-prescribed fluid loss rate input FLRin. Scale input Ws may be transmitted from the substitution scale 49 via the transmitter 51. Scale input Wf may be transmitted from the filtrate scale 35 via the transmitter 37. The specified input SFRin may be input through the user interface 61, or it may be input from another source 65, such as a predetermined value stored in a memory or calculated by an appropriate software module. The prescribed input FLRin may be input through the user interface 61, or it, too, may originate from another memory or software module 67. The four outputs are substitution flow rate control signal SFRout, filtrate flow rate control signal FFRout, high total fluid loss alarm TFL-h and low total fluid loss alarm TFL-l.

The flow controller module 71 can generate output signal SFRout that drives the substitution fluid pump 41. The flow controller module 71 can drive the pump 41 according to control signal X generated by the control module 73, or according to override signal OVR received by reading a value stored in a memory module 63. Similarly, flow controller module 69 can generate output signal FFRout that drives the filtrate fluid pump 29. The flow controller module 69 can drive the pump 29 according to control signal Y generated by the control module 73, or according to override signal OVR received by reading memory module 63. Signal FFRin may be generated by filtration flow calculator module 75.

The filtration flow calculator module 75 may calculate signal FFRin based on two inputs: SFRin and FLRin. In one embodiment, the filtration flow calculator module 75 calculates FFRin as the difference between FLRin and SFRin, or FFRin=FLRin−SFRin. In other words, the desired value for filtrate flow rate is determined to be the difference between a prescribed fluid loss rate and a specified substitution fluid flow rate. Thus, if a patient is prescribed an FLR of zero (i.e., no net gain or loss of fluid), then the amount of filtrate removed from the circuit should ideally equal the amount of substitution fluid added to the circuit. In other embodiments, the filtration flow calculator module 75 may perform a calculation based on more than two inputs. For example, in hemodiafiltration therapies or other types of extracorporeal circuits having multiple sources of fluid addition and/or multiple sinks of fluid subtraction, the calculation executed by the filtration flow calculator module 75 takes at least as many variables into account as there are sources or sinks in the circuit. A circuit having both a pre-dilution substitution pump and a post-dilution substitution pump is one such circuit. A circuit pumping a dialysate through the hemofilter is another.

The flow controller modules 69 and 71 decide how to drive their respective pumps according to actual fluid measurements taken during the course of therapy. These measurements are taken by the filtrate scale 35 and the substitution fluid scale 49. During therapy, as substitution fluid is added to the circuit, the amount of substitution fluid contained in the substitution fluid container 45 is depleted. The rate of depletion may be measured by the substitution fluid scale 49 taking weight measurements over a time period T. These measurements may be transmitted to the controller 11 as feedback signal Ws. In one embodiment, Ws is an analog signal received in the controller 11 by analog-to-digital (A/D) converter module 79. The A/D converter module 79 converts Ws to a digital signal S for input to differencing module 81. In another embodiment, Ws may be transmitted as digital signal S directly from the substitution fluid scale 49 without the need for A/D conversion. During the same therapy session, as filtrate is removed from the circuit, the amount of filtrate removed is collected in filtrate container 33. The rate of accumulation of filtrate may be measured by scale 35 taking measurements over time period T. These measurements may be transmitted to the controller 11 as feedback signal Wf. For analog transmission, Wf may be received in the controller 11 by the A/D converter module 77, which converts Wf into digital signal F for input to differencing module 81. In another embodiment, F may be transmitted directly from scale 35 as a digital signal.

The differencing module 81 compares signals F and S and outputs the difference between them. In one embodiment, a differential amplifier circuit may be used for this purpose. The output of the differencing module 81 is the difference signal FLR-actual, which represents the actual fluid loss rate through the extracorporeal circuit. This value is fed to comparator module 83 for comparison to the prescribed fluid loss rate FLRin originating from the user interface 61 or the fluid loss rate input module 67.

The comparator module 83 compares FLR-actual to FLRin to produce an error signal $\Delta$FLR, and may transmit error signal $\Delta$FLR as feedback to the control module 73. The control module 73 may generate control signal X for driving the substitution fluid pump 41, and control signal Y for driving the filtrate pump 29. The control signal X may be calculated based on SFRin, and adjusted responsive to error signal $\Delta$FLR in order to eliminate the error. Similarly, the control signal Y may be calculated based on signal FFRin received from the filtration flow calculator module 75, and adjusted responsive to error signal $\Delta$FLR to eliminate the error. Any number of known algorithms for controlling process variables may be used in the control module 73 for these purposes, such as proportional, integral, or derivative control algorithms, or any combination thereof. In another embodiment, the control module 73 may employ a state-space control algorithm. The X and Y control signals may be fed to flow limiters 71 and 73, respectively, which, in the absence of an override signal, may relay the respective control signal to the substitution fluid pump 41 or the filtrate pump 29, as the case may be. In this way, subject to an override condition, the control module 73 controls the speed of the pumps 29 and 41, and hence, the respective flow rates of the substitution fluid and filtrate in the extracorporeal circuit.

An override condition exists when TFL drifts outside a predetermined tolerance range. For example, for hemofiltration therapy administered to an adult patient, the tolerance range may be set +/−50 g of fluid, although any desired range may be used. For hemofiltration therapy administered to a child patient, the tolerance range may be set more narrowly, for example, at +/−20 g. The high and low set points that define the tolerance range may be preset, or may be input by a user through the user interface 61. An out-of-tolerance condition may be detected by integrating the $\Delta$FLR error signal and comparing it to these predetermined set points. In one embodiment, the comparator 83 may output error signal $\Delta$FLR to an integrator module 85. At the integrator module 85, the error signal may be integrated from time t=0 (e.g., at therapy start-up) to maintain a current value for TFL over the course of an uninterrupted session of therapy. In one embodiment, the TFL value may be periodically stored in TFL memory 63. In another embodiment, the TFL value stored in the TFL memory 63 may overwrite any previously stored TFL value.

In another embodiment, if the TFL value reaches a predetermined low set point, integrator module 85 may store the value in the TFL memory 63 and transmit TFL-l (low total fluid loss) alarm signal as an output to low TFL alarm 87. The alarm may inform a user of the low fluid condition, which may indicate a problem in the circuit such as a leak, an occluded fluid line, a pump malfunction, or an empty substitution fluid bag. Similarly, if the TFL value reaches a predetermined high set point, integrator module 85 may store the value in the TFL memory 63 and transmit TFL-h (high total fluid loss) alarm signal as an output to high TFL alarm 89. A high TFL alarm may indicate a high fluid condition and alert the user to a problem such as a clogged hemofilter, a pump malfunction, an occluded filtrate line, or a filtrate bag filled to capacity.

In one embodiment, if the TFL value reaches either a low set point or a high set point, flow limiters 69 and 71 may receive OVR signals causing all pumps to shut down. In this case, therapy may be interrupted and the system turned off until administratively reset by a user. This allows the user an opportunity to rectify the condition that caused TFL to drift out of tolerance. Upon re-start, the flow limiters 69 and 71 may initially check the TFL memory 63 for a TFL out-of-tolerance condition, and if such condition is detected, operate only one pump until a desired fluid balance is achieved. For example, if at re-start TFL is out-of-tolerance high, the flow limiter 71 may override the control signal X by stopping the substitution fluid pump 41, while the flow limiter 69 may override the control signal Y by running the filtrate pump 29 at a predetermined speed. If at re-start TFL is out-of-tolerance low, the flow limiter 71 may override the control signal X by running the substitution fluid pump 41 at a predetermined speed, while the flow limiter 69 may override the control signal Y by stopping the filtrate pump 29. When a desired fluid balance is achieved, OVR signals are removed and the flow limiters 69 and 71 may transmit the X and Y control signals as output to the pumps 41 and 29, respectively. In one embodiment, when the desired fluid balance is restored, a timer (not shown) may be reset to time t=0 to reinitialize TFL calculation by the integrators 85.

In another embodiment, if the TFL value reaches either a low set point or a high set point, the system may enter an override state and continue running. In such an override state, the flow limiters 69 and 71 may receive OVR signals that selectively turn pumps on and off. For example, if the TFL value reaches a low set point, the flow limiter 71 may continue to output control signal X to the substitution fluid pump 41, while the flow limiter 69 may receive an OVR signal causing it to stop the filtrate pump 29. In the case of TFL reaching a high set point, the flow limiter 71 may receive an OVR signal to stop the substitution pump 41, while the flow limiter 69 may continue to output control signal Y to the filtrate pump 29. In any of these override states, the feedback signals from the scales 35 and 49 may continue to be received by the controller 11, so that the integrators 85 may continue updating and storing TFL values. In one embodiment, an override state exists until a desired fluid balance is achieved, e.g., TFL=0. At that point in time, the OVR signals may be removed, time t may be reset to zero, and the flow limiters 69 and 71 may return to normal operation. In normal operation, control signals X and Y are output to the pumps 41 and 29, respectively.

With integrators continually or periodically updating TFL and storing the same in non-volatile TFL memory, a system according to the invention may recover from an interruption in therapy without losing track of the patient's TFL. There are many reasons an interruption may occur. For example, the interruption may occur as a result of loss of electrical power. In other cases, an interruption may be necessary to allow health care professionals to attend to other needs of the patient, to perform maintenance on the hemofiltration system, to clear an alarm, or to follow a prescribed profile for non-consecutive sessions of therapy. Whatever the reason for interrupting therapy, the invention allows the system to be restarted and therapy to be resumed without accumulating TFL errors in subsequent sessions. In one embodiment, upon restarting therapy, the system may first check the TFL value stored in the TFL memory 63, and if the TFL is non-zero, the system may enter an override state until a desired TFL is achieved. In another embodiment, the system on restart may assume normal operation as long as TFL is not out of tolerance, and begin integrating TFL, using the stored TFL value as an initial value. In another embodiment, alarm TFL-l or TFL-h may be activated by the controller 11 upon system start-up or restart, if a stored value for TFL is out of tolerance.

Figure 3:
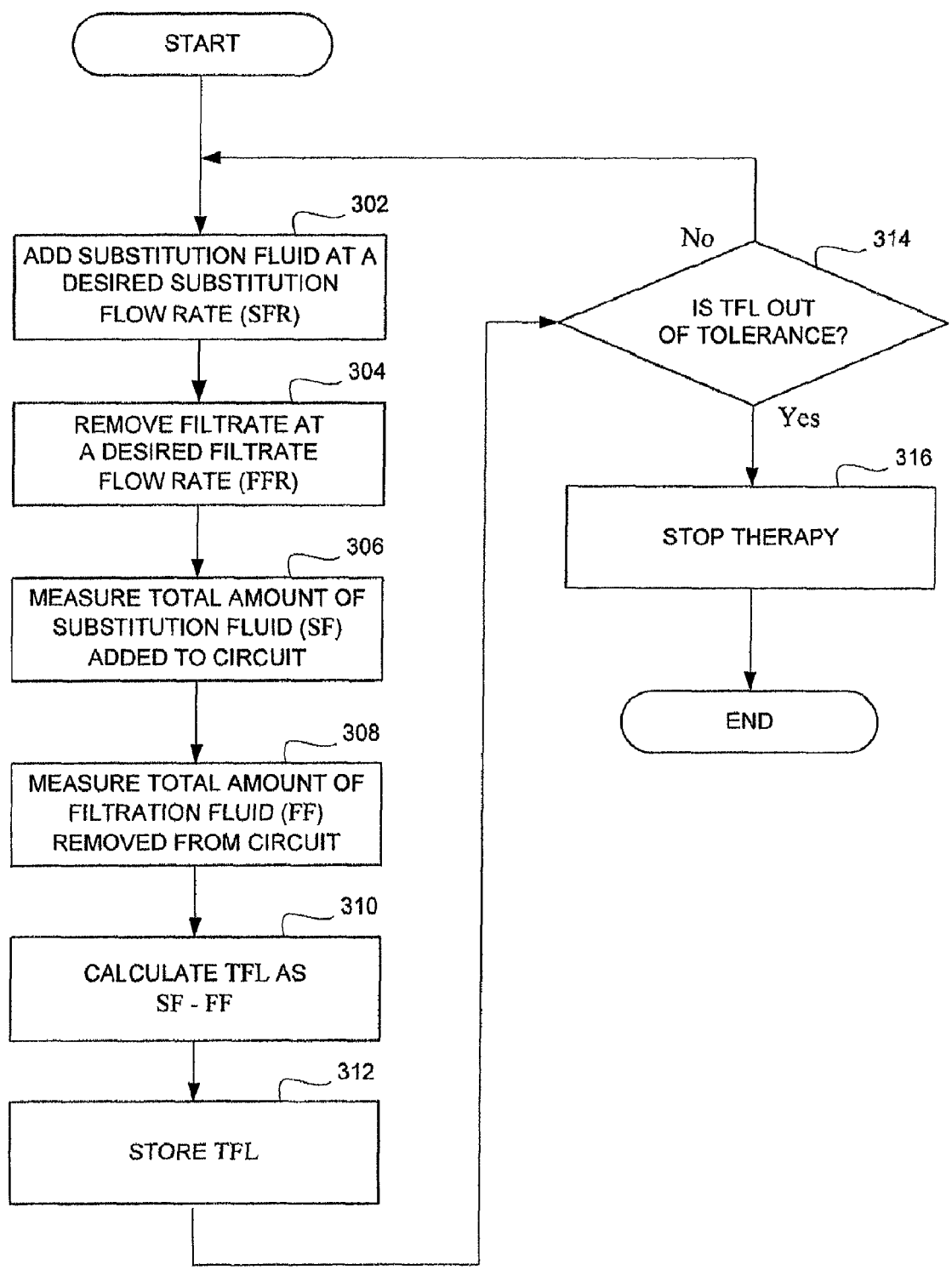
FIG. 3 is a flow diagram embodying a method for controlling TFL according to an embodiment of the invention.

With the aforedescribed system embodiments in mind, embodiments of methods according to the invention for controlling TFL are now described. FIG. 3 illustrates one such embodiment as a series of steps of method 300 modeled in a process flow chart. The process may be employed during any hemofiltration, plasmapheresis, renal replacement therapy or fluid-management therapy.

The first step is shown in process block 302. In this step, substitution fluid is added to an extracorporeal hemofiltration circuit at a desired substitution fluid flow rate. This step involves a user specifying the substitution fluid flow rate using an input device such as a user interface, or it may involve turning on one or more pumps. The second step is step 304. This step involves removing filtrate from the same hemofiltration circuit at a desired filtrate flow rate. This step involves a user specifying a desired filtrate flow rate using an input device, or it may involve turning on a filtrate pump. In another embodiment this step may involve a user inputting a prescribed fluid loss rate.

The next step in method 300 is step 306. In step 306, the total amount of substitution fluid (S) added to the hemofiltration circuit is measured. There are many ways to take this measurement. For example, a flow totalizer may be used to keep track of substitution fluid entering the circuit. Another example discussed above in system embodiments uses a scale to measure the change in weight of substitution fluid. In the next step 308, of the total amount of filtrate (F) removed from the circuit is measured. This step may also be accomplished using scales or another appropriate instrument.

In the next step 310, a calculation is performed to determine TFL. In one embodiment, TFL is calculated as: TFL=S−F. Where multiple sources add fluid to the circuit, or where multiple sources sink fluid from the circuit, the calculation performed in step 310 may account for more variables. Once TFL is determined, the method proceeds to step 312. In step 312, the value of TFL calculated in the previous step is stored in retrievable memory.

The next step 314 is a decision block. Here, the value for TFL is compared to a predetermined tolerance range. If the value for TFL is determined to lie within the range, then the method loops back to step 302, and therapy continues. If, however, the value for TFL is determined to lie outside the range, then the method proceeds to the final step 316. In step 316, therapy is stopped. One example of performing step 316 is issuance of a command or action that causes all fluid pumps in the circuit to shut off.

Figure 4:
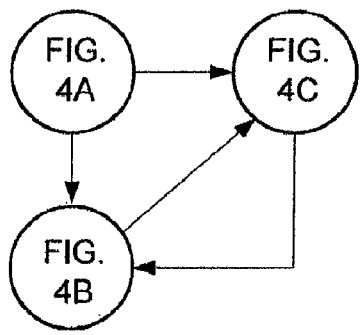
FIG. 4 (includes FIGS. 4A, 4B and 4C) is a flow diagram embodying a method for controlling TFL according to an embodiment of the invention.

FIG. 4 illustrates another embodiment of a method 400 for controlling TFL during hemofiltration therapy. FIG. 4 includes FIG. 4A, FIG. 4B, and FIG. 4C, as shown diagrammatically, and method 400 comprises the process steps shown in all of these figures. Method 400 may be employed using a control system for an extracorporeal hemofiltration circuit that may include one or more fluid pumps and feedback instrumentation as shown in the above system embodiments.

Figure 4A:
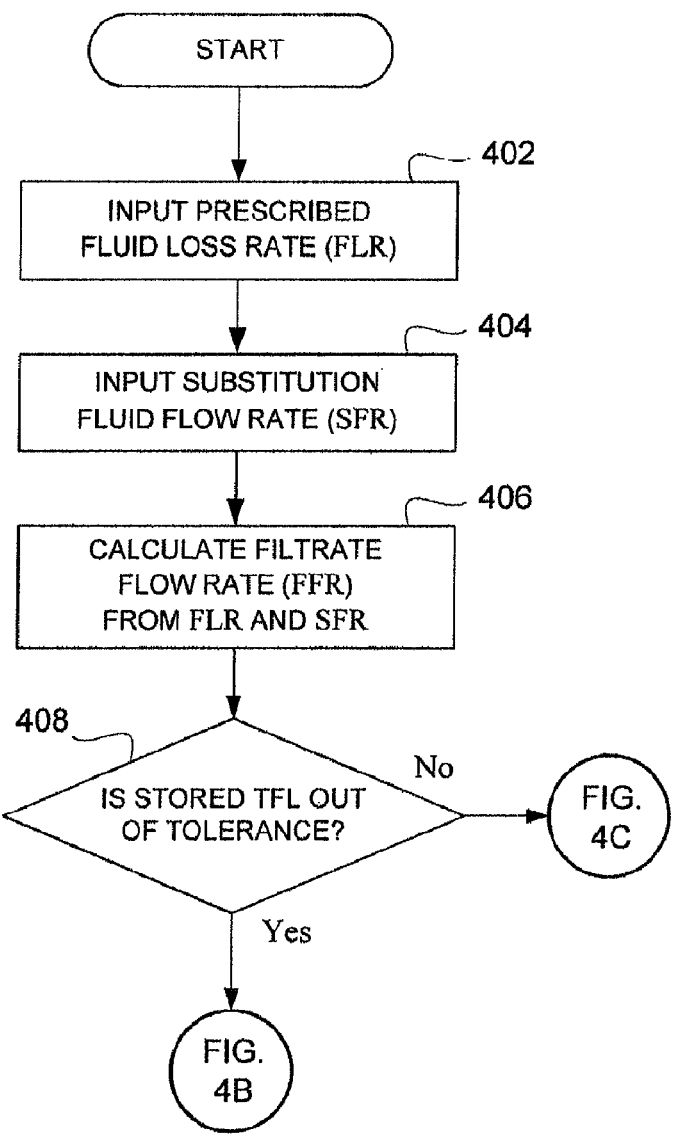
FIG. 4A illustrates a first portion of the method of FIG. 4 including steps for initial user inputs and initial determination of TFL falling within a prescribed tolerance range according to an embodiment of the invention.

The first step in method 400 is step 402 shown in FIG. 4A. This step may be executed upon starting a first therapy session, or it may be executed after an interruption of a previous therapy session in order to continue therapy. In this initial step, a prescribed fluid loss rate (FLR) is input to a hemofiltration system. In a broad sense, this step may represent a value for FLR being prescribed by a health care professional for a patient undergoing hemofiltration therapy. In one embodiment, FLR may be input to a control system using a computer keyboard or other user interface. Where no net gain or loss of fluid is prescribed during therapy, FLR may be input as zero. In the absence of an input action, setting a default value of FLR equal to zero may be considered as accomplishing this initial step. In another embodiment, this step may represent retrieving a prescribed FLR value from a memory, where the value was stored during a previous therapy session.

The next step in the method is 404, in which a value is input for substitution fluid flow rate (SFR). This step may include inputting into the hemofiltration control system a specified value for SFR that lies within a normal operating range of the substitution fluid pump. In another embodiment, this step may include operating such a pump at a rated speed. With FLR and SFR established in the two preceding steps, a calculation for filtrate flow rate (FFR) is performed next in step 406. In this step, FFR may be calculated based oil FLR and SFR. In one embodiment, FFR is calculated as the difference between FLR and SFR.

The next step 408 is a decision block in which the stored value for TFL is read and compared to a predetermined tolerance range. The value of TFL may be zero at first execution of step 408, i.e., at the beginning of patient therapy. However, upon starting a subsequent therapy session for the same patient, the value of TFL retrieved from memory may be non-zero. If the stored value for TFL is within the tolerance range, the method proceeds to step 432 of FIG. 4C. However, if the stored value for TFL is outside the tolerance range, then the method proceeds to step 410 of FIG. 4B.

Figure 4B:
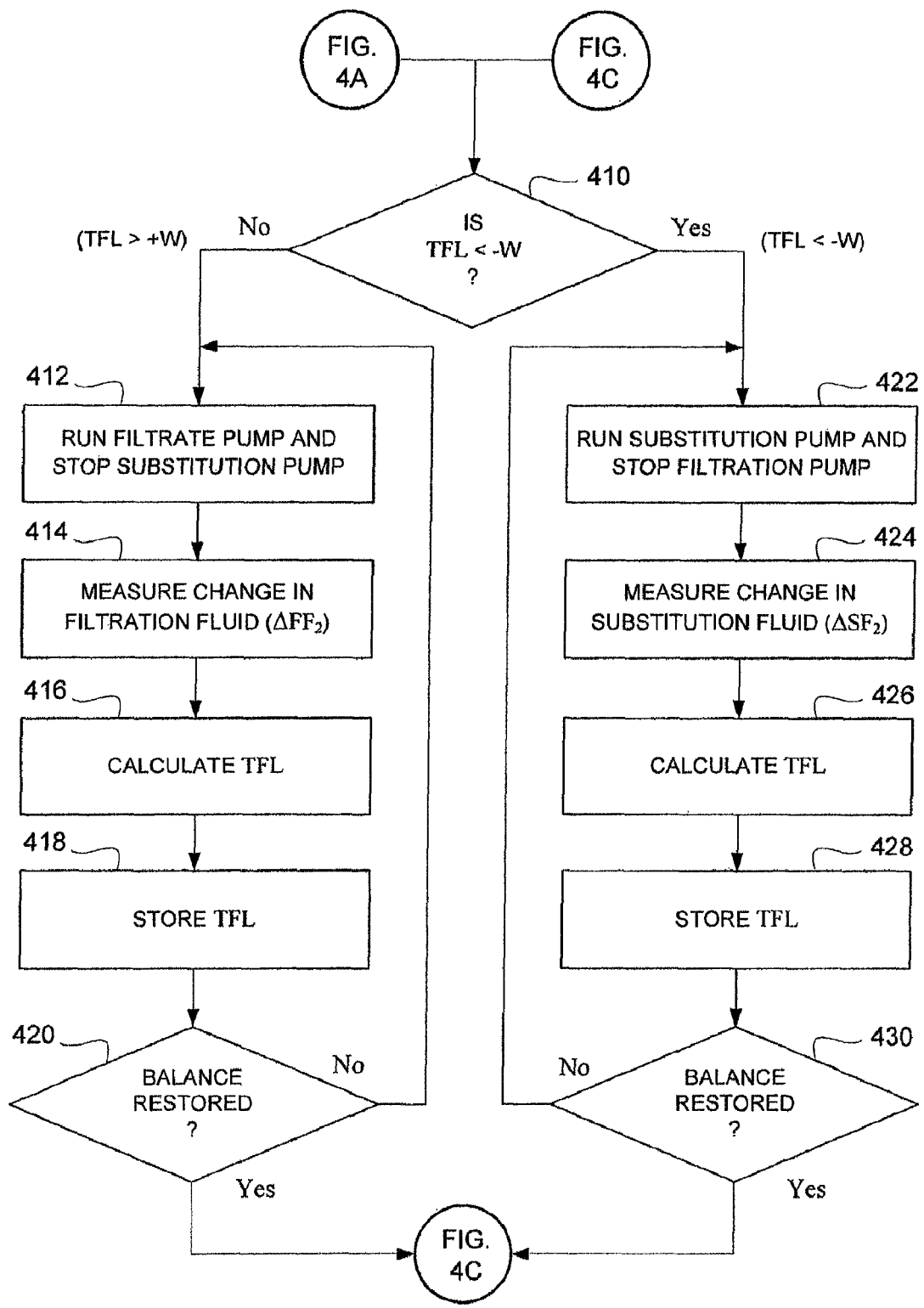
FIG. 4B illustrates a second portion of the method of FIG. 4 including steps for restoring fluid balance if TFL is detected out of tolerance according to an embodiment of the invention.

Turning now to FIG. 4B, step 410 may be performed when TFL is determined to be out of tolerance. Step 410 is another decision block. It may determine whether TFL is out-of-tolerance high (TFL>+W) or out-of-tolerance low (TFL<−W). If TFL is out-of-tolerance high, i.e., if TFL is equal to or higher than the high set point +W, the method proceeds to step 412.

In step 412, the filtrate pump or pumps may be turned on (or allowed to continue running) and all substitution fluid pumps, dialysate pumps, and other pumps adding fluid to the circuit may be stopped. Next, in step 414, measurements may be taken to determine the change in the amount of filtrate removed ($\Delta F_1$) from the circuit since determining TFL out of tolerance. These measurements may be taken, for example, by measuring flow over a time interval, or by weighing filtrate collected in the filtrate container 33 at two or more time intervals. After a time interval, step 416 may be performed. In step 416, a new value for TFL may be calculated based on the most recent measurement of filtrate. The calculation may be made using a suitable equation or algorithm. In one embodiment, TFL may be calculated as TFL=TFL (stored)−$\Delta F_1$. In the next step 418, the new value of TFL calculated in step 416 is stored as an updated TFL value. The next step is decision block 420. In block 420, it may be determined whether the updated TFL value indicates that fluid balance in the patient has been restored, i.e., whether the updated value of TFL equals a prescribed value of TFL, such as zero. In one embodiment, when removing filtrate, the fluid balance is attained when the volume of filtrate removed from the circuit (after determining TFL out of tolerance) equals the out-of-tolerance value of TFL. If balance is restored, the method may then proceed to step 432 of FIG. 4C. If not, the method may loop back to step 412.

Returning now to step 410, if TFL is out-of-tolerance low, i.e., if TFL is less than the low set point −W the method proceeds to step 422. In step 422, the substitution fluid pump or pumps may be turned on (or allowed to continue running) and all filtrate pumps and other pumps removing fluid from the circuit may be stopped. Next, in step 424, measurements may be taken to determine the change in the amount of substitution fluid removed ($\Delta S_1$) from the circuit since determining TFL out of tolerance. These measurements may be taken using any of the same techniques used for measuring filtrate. After a time interval, step 426 may be performed. In step 426, a new value for TFL is calculated based on the most recent measurement of substitution fluid. The calculation may be made using a suitable equation or algorithm. In one embodiment, TFL may be calculated as TFL=TFL (stored)+$\Delta S_1$. In step 428, the new value of TFL calculated in step 426 may be stored as an updated TFL value. In step 430, it may be determined whether the updated TFL value indicates that fluid balance in the patient has been restored. In one embodiment, when adding substitution fluid, the fluid balance is attained when the volume of substitution fluid added to the circuit (after determining TFL out of tolerance) equals the out-of-tolerance value of TFL. If balance is restored, the method may then proceed to step 432 of FIG. 4C. If not, the method may loop back to step 422.

When the method reaches step 432, TFL has ideally achieved a desired fluid balance. At this point, step 432 may be executed to reset a time period for calculating TFL. In one embodiment, this may include resetting or initializing a time counter, or resetting the time to t=0. With the time counter initialized, the method proceeds to step 434. In step 434, substitution fluid pumps and filtrate pumps may be run according to SFR and FFR, as input or calculated in steps 404 and 406, respectively. The next two steps are measurement steps. In step 436, the change in substitution fluid added to the circuit ($\Delta S_2$) may be measured, and in step 438, the change in filtrate removed from the circuit ($\Delta F_2$) may be measured. The measurements taken in these two steps may be taken over any suitable time period $\Delta T$.

The next step is a calculation step 440, which may be a step for calculating TFL from time t=0, i.e., from the time reset in step 432. In one embodiment, this calculation may compute TFL over time period $\Delta T$ as the difference between $\Delta S_2$ and $\Delta F_2$, plus an updated value for TFL. In another embodiment, this calculation may integrate or otherwise sum up all $\Delta S_2$ and $\Delta F_2$ over a time interval greater than $\Delta T$ to determine S and F, compute the difference between S and F, and add this difference to an updated value for TFL. In any case, the TFL value calculated in step 440 may represent the actual TFL since the reset time t=0. In step 442, the TFL value calculated may be stored as an updated value for TFL.

Step 444 compares the value for TFL updated in the immediately preceding step to a predetermined tolerance range, where the range has an upper set point limit of +W and a lower set point limit of −W. If TFL is determined to lie within this range, the method proceeds to step 446. If not, the method may loop back to step 410 of FIG. 4B.

The next two steps represent optional controlling steps where an error signal may be calculated and used as feedback for maintaining fluid flow rates under control. First, in step 446, a UF variation error signal ($\Delta UF$) may be calculated by measuring in a differential time period $\Delta P$, the difference between the prescribed fluid loss ($\Delta FLR$) during $\Delta P$, plus a differential volume of fluid removed ($\Delta F_2$) from the circuit during $\Delta P$, minus the differential volume of fluid added ($\Delta S_2$) to the circuit during $\Delta P$. The error may be expressed algebraically as:

$$\Delta UF = \Delta FLR + \Delta F_2 - \Delta S_2$$

In one embodiment, $\Delta F_2$ represents a differential change in filtrate volume removed from the circuit, and $\Delta S_2$ represents a differential change in substitution fluid volume added to the circuit. In another embodiment, $\Delta S_2$ may include a differential change in anticoagulant solution. In another embodiment, $\Delta S_2$ may include a differential change in dialysate fluid.

In step 448, SFR and FFR are adjusted in response to error signal $\Delta UF$ to drive the error to zero. There are many ways to accomplish this step. In one embodiment, $\Delta UF$ may be transmitted as negative feedback to a control algorithm, which in turn adjusts its output so that drive signals SFR and FFR converge to a desired value. A state-space control algorithm, or an algorithm using proportional, integral, or derivative control, or a combination thereof, may be employed in this step.

Step 450 determines whether a prescribed therapy has been completed. If not, the method may loop back to step 434. If so, the process ends. In determining whether therapy is complete, step 450 may compare a variable under measurement to pre-determined criteria, and end the process if the criteria is satisfied. For example, step 450 may include comparing a time count to a prescribed elapsed time. In another example, step 450 may include comparing TFL to a prescribed total fluid loss. In another embodiment, step 450 may terminate the process when prescribed blood chemistry is achieved.

Note that through any of the loops of method 400, the value for TFL is frequently calculated and stored. Thus, if therapy is interrupted during any process step, the value of TFL stored in retrievable memory represents a highly accurate measurement of the state of actual fluid loss in a patient at the time of interruption. This enables therapy to be resumed after one or more interruptions, whether due to power loss or to an administrative shut-down, without fear of accumulating uncorrected TFL errors.

The flow chart of FIG. 5 illustrates some optional steps in a method for controlling TFL during hemofiltration therapy. These are initialization steps 403, 405, and 407, which may occur during execution of method 400, preferably after start and prior to decision block 408. The initialization steps may occur in any order, as indicated by the dashed flow lines of FIG. 5. Each of these steps call for an automatic or manual input for the specification or selection of a value for a control parameter. An automatic input may be a default value. A manual input may be effected, for example, by a health care professional specifying a value in response to a software prompt via a user interface such as a mouse or keyboard.

In initialization step 403, the stored value for TFL may be set to a desired value, which is typically zero. A zero value for TFL indicates an initial balanced fluid condition in a patient. An initial value for TFL may also be input as a non-zero value, to reflect a known fluid imbalance at start. In initialization step 405, a value W may be input or selected to set a tolerance setpoint, or discrepancy offset limit, for TFL. In one embodiment, both high and low tolerance set points may be selected to have different absolute values. In initialization step 407, a value Tmax may be input or selected to set a maximum duration for operating the total fluid loss control system in an out-of-tolerance condition. This is a safety feature for ensuring that an uncorrectable out-of-tolerance condition is not made worse by a system defect such as an inoperable pump or a leak in a fluid line. Tmax may be set to any desired value, and may vary according to the type of hemofiltration therapy being administered. For example, Tmax may be specified on the order of minutes, tens of minutes, or hours.

Figure 4C:
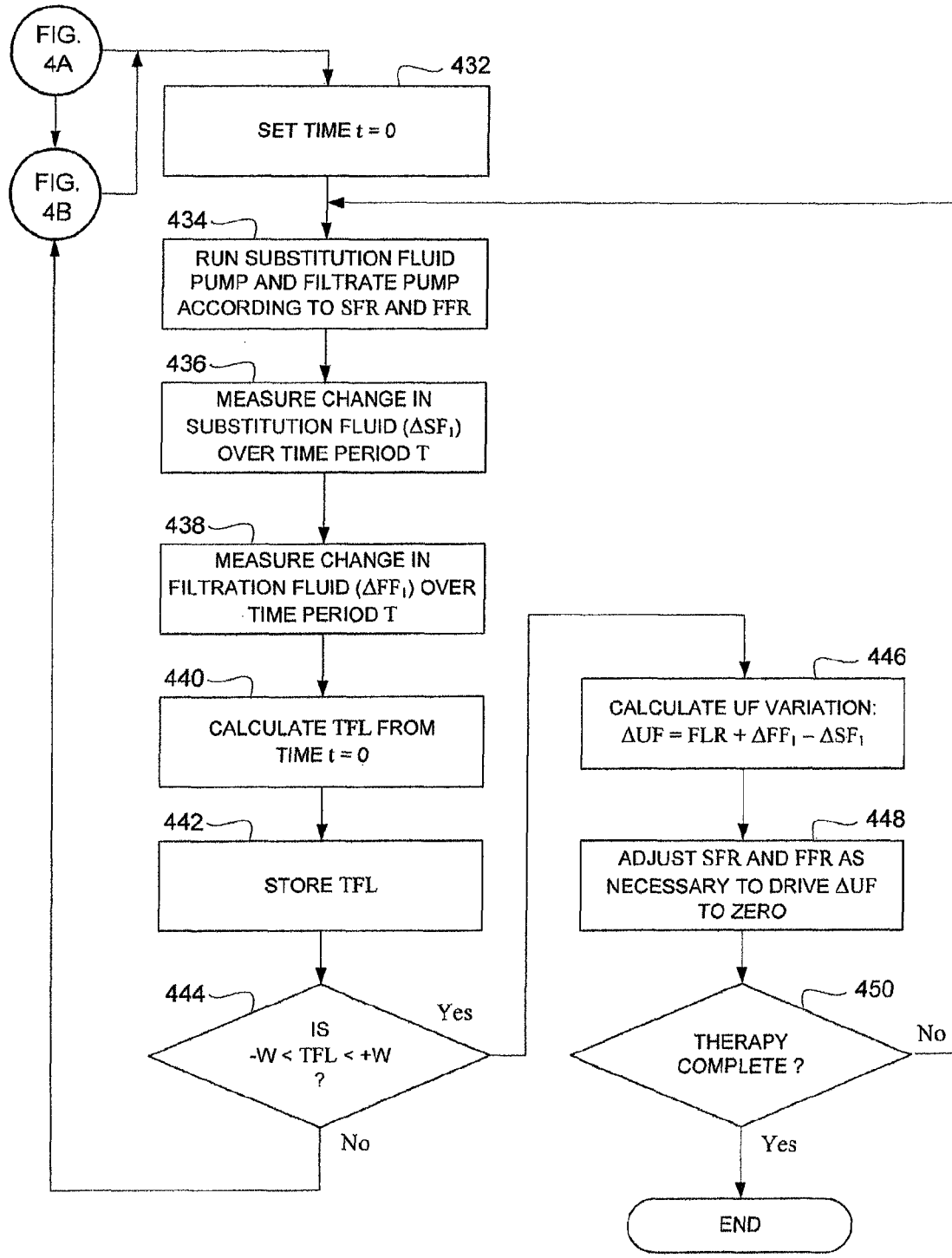
FIG. 4C illustrates a third portion of the method of FIG. 4 including steps for calculating TFL and steps for correcting flow rates during system operation when TFL lies within a prescribed tolerance range according to an embodiment of the invention.

FIG. 6 illustrates a process or algorithm for implementing the Tmax safety feature. The algorithm may be added as a series of steps within method 400, beginning at step 444. Step 444 decides whether the stored value for TFL is in or out of tolerance, by comparison to the tolerance set points −W and +W. If TFL is out of tolerance, the algorithm proceeds to process step 445, which starts a timer to keep track of how long the out-of-tolerance condition remains uncorrected. In the next step 447, the algorithm determines whether the elapsed time representing the duration of the out-of-tolerance condition exceeds Tmax. If not, the algorithm proceeds to step 446, as shown in FIG. 4C. If so, the hemofiltration therapy is immediately stopped at the next step 449. In one embodiment, step 449 may be accomplished by the controller 11 interrupting power to the pumps 19, 29, and 41. In another embodiment, only the filtrate pump 29 and the substitution fluid pump 41 are stopped in step 449. In another embodiment, all pumps except for the blood pump 19 are stopped in step 449. System maintenance or other manual action may be required to effect a re-start.

Figure 7:
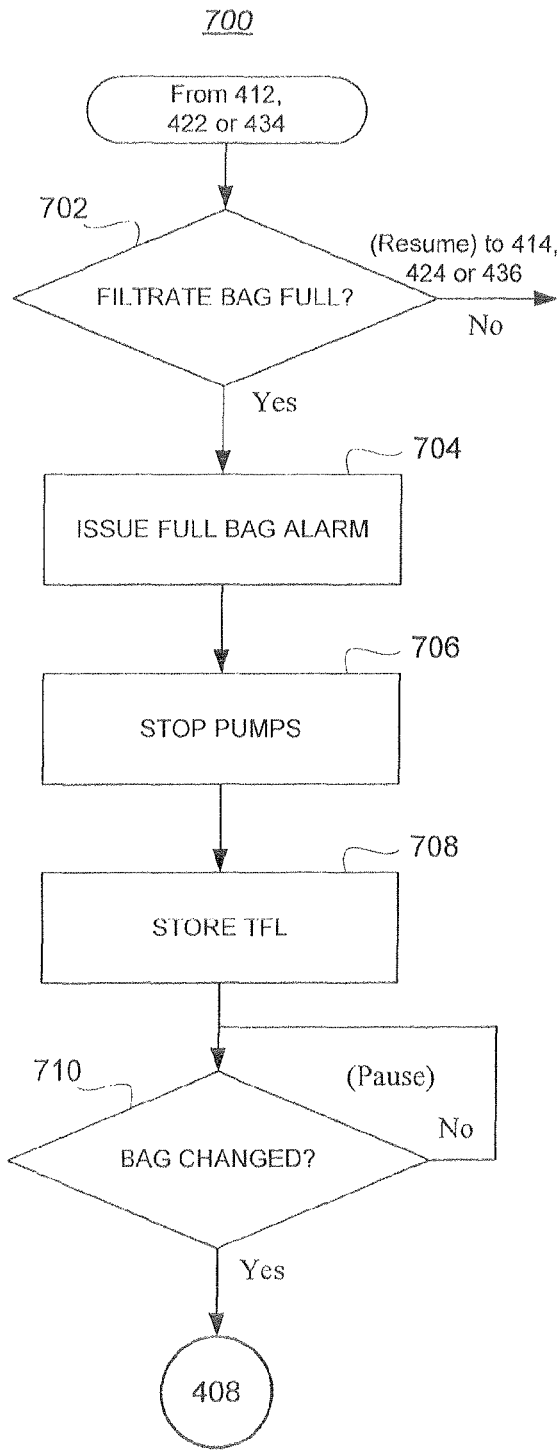
FIG. 7 is a flow chart illustrating optional steps in a method for preserving stored information during interruption of hemofiltration therapy to allow maintenance to the extracorporeal circuit according to an embodiment of the invention.
Figure 8:
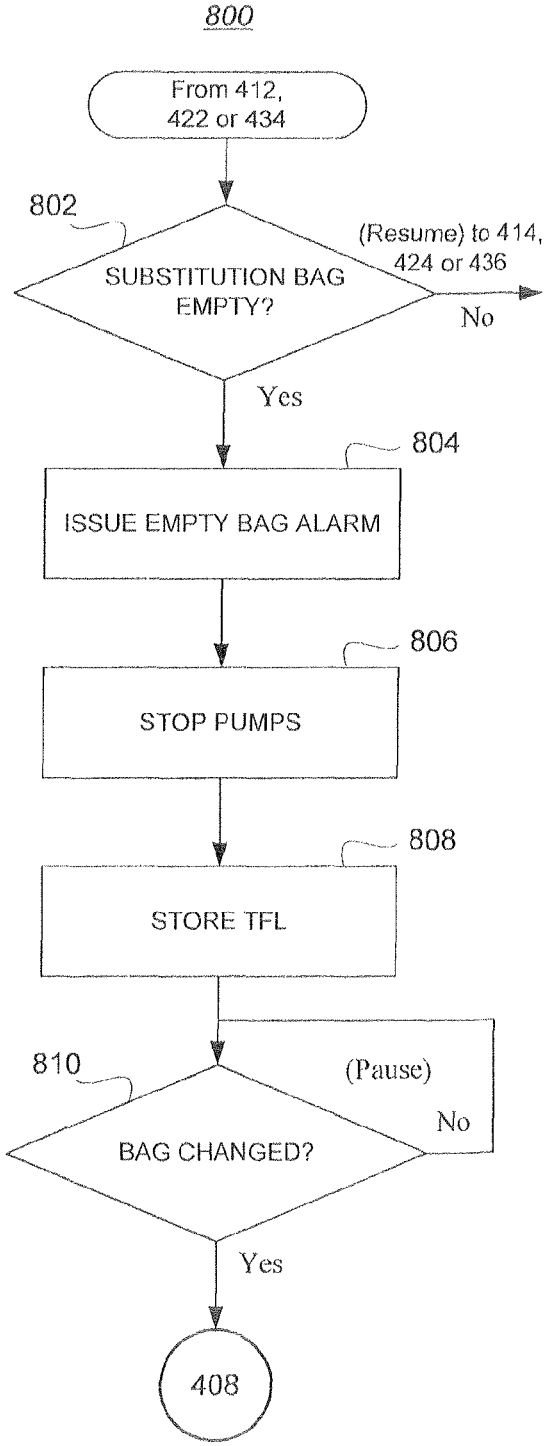
FIG. 8 is another flow chart illustrating optional steps in a method for preserving stored information during interruption of hemofiltration therapy to allow maintenance to the extracorporeal circuit according to an embodiment of the invention.

FIG. 7 and FIG. 8 illustrate additional steps that may be added as process loops in an algorithm or method according to the invention. These loops may be needed especially for prolonged therapy that may likely require the replacement of one or both of the filtrate collector 33 and the fluid container 45, or for other maintenance of the extracorporeal circuit. When filtrate collector 33 becomes full, or when fluid container 45 becomes empty, the hemofiltration system is designed to interrupt the therapy to allow for bag replacement without losing track of TFL. Loop 700 interrupts therapy in response to a full filtrate collector. Loop 800 interrupts therapy in response to an empty container of substitution fluid. Either or both of these loops may be implemented prior to or after a pump running step (e.g., step 412, 422, or 434) to ensure interruption of therapy when bag replacement is required.

Loop 700 begins at step 702, which is a decision block that determines whether the filtrate bag or collector is full. This decision may be resolved by the controller 11 reading a signal from the transmitter 37. If the filtrate bag is determined not to be full, the process departs loop 700 by returning to the main algorithm to resume operation right where it left off. For example, if the main algorithm entered loop 700 from step 412, it would resume at step 414. If it entered from step 422, it would resume at step 424. If it entered from step 434, it would resume at step 436. If, however, the filtrate bag is determined to be full, step 704 is executed to issue a full bag alarm. The filtrate alarm 39 may be actuated during this step. In the next step 706, one or more of the pumps are stopped. In one embodiment, only the filtrate pump 29 is stopped. In another embodiment, the blood pump 19 may continue to operate after issuance of the alarm.

In the next step 708, the current value of TFL is stored in memory. Loop 700 pauses operation of the system until the filtrate collector is changed. This pause is illustrated using decision block 710, which remains in an indefinite loop until there is a positive indication of a bag change. When a new filtrate collector has been installed, the method proceeds to step 408 for evaluation of TFL. Positive indication of a bag change may be indicated to the controller 11, for example, using microswitch technology and appropriate logic.

The steps of loop 800 are for monitoring the state of substitution fluid, using logic similar to that of loop 700. In loop 800, step 802 determines whether the substitution fluid bag or container is empty. This decision may be resolved by the controller 11 reading a signal from transmitter 51. If the substitution fluid container is determined not to be empty, the process departs loop 800 by returning to the main algorithm to resume operation right where it left off. For example, if the main algorithm entered loop 800 from step 412, 422, or 434, it would resume at step 414, 424, or 436, respectively. If, however, the substitution fluid container is determined to be empty, step 804 is executed to issue an empty bag alarm. The substitution fluid alarm 53 may be actuated during this step. In the next step 806, one or more of the pumps are stopped. In one embodiment, only the substitution fluid pump 41 is stopped. In another embodiment, the blood pump 19 may continue to operate after issuance of the alarm.

In the next step 808, the current value of TFL is stored in memory. Loop 800 pauses operation of the system until the substitution fluid container is changed. This pause is illustrated using decision block 810, which remains in an indefinite loop until there is a positive indication of a bag change. When a new substitution fluid container has been installed, the method proceeds to step 408 for evaluation of TFL. Positive indication of a bag change may be indicated to the controller 11 by the transmitter 51 detecting the bag weight, or through other appropriate logic.

The invention has been disclosed in an illustrative manner. Accordingly, the terminology employed throughout should be read in an exemplary rather than a limiting manner. Although minor modifications of the invention will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A system for administering a blood treatment therapy comprising:
    a substitution fluid pump;
    a filtrate pump;
    controller for managing fluid flow of a treatment using the substitution fluid pump and the filtrate pump, the controller including
        (i) a plurality of inputs, including an actual substitution fluid input, an actual filtration input, a prescribed substitution fluid input and a prescribed filtration input,
        (ii) a plurality of outputs, including a substitution fluid flow output, a filtration flow output, a high total fluid loss alarm output and a low total fluid loss alarm output,
        (iii) a differencing module configured to provide an actual flow difference signal calculated as the difference between the actual substitution fluid input and the actual filtration input,
        (iv) a comparator configured to compare the actual flow difference signal to: (a) the prescribed substitution fluid flow input, and (b) the prescribed filtration flow input to (c) produce a flow error signal,
        (iv) a total fluid loss module configured to calculate and store a total fluid loss value based upon the flow error signal, wherein the total fluid loss module outputs: (a) the high total fluid loss alarm signal if the total fluid loss value is above an upper threshold, (b) the low total fluid loss alarm signal if the total fluid loss value is below a lower threshold, and (c) an override signal if the total fluid loss value is within the upper and lower thresholds; and
    wherein the substitution fluid flow output and the filtration flow output are adjusted based at least in part upon the flow error signal and the override signal.

2. The system of claim 1, wherein the controller is further configured to update the total fluid loss value stored in the total fluid loss module based upon a change in the actual substitution fluid input or the actual filtration input.

3. The system of claim 2, wherein the controller is further configured to update the substitution fluid flow output or the filtration flow output based upon the updated total fluid loss value.

4. The system of claim 1, which is configured to calculate and store the total fluid loss value for a particular time of the treatment.

5. The system of claim 1, wherein the controller is further configured to retain the total fluid loss value upon a loss of electrical power to the system.

6. The system of claim 5, wherein when the system restarts after the loss of electrical power, the controller retrieves the last stored total fluid loss value from the total fluid loss module.

7. The system of claim 6, wherein if upon restart the total fluid loss value is above the upper threshold or below the lower threshold, the controller is configured to adjust at least one of the substitution fluid flow output and the filtration flow output until the total fluid loss value is within the thresholds.

8. The system of claim 1, wherein at least one of the actual substitution fluid input, actual filtration input, prescribed substitution fluid input, prescribed filtration input, substitution fluid flow output, filtration flow output, actual flow difference signal, flow error signal, or total fluid loss value is a rate input, rate output, rate signal or rate value, respectively.

9. The system of claim 1, wherein if the total fluid loss value is above the upper threshold or below the lower threshold, the controller is configured to adjust at least one of the substitution fluid flow output and the filtration flow output until the total fluid loss value is within the thresholds.

10. The system of claim 1, wherein if (a) the high total fluid loss alarm signal or (b) the low total fluid loss alarm signal is outputted, the controller ceases operation of at least one of the substitution fluid pump and the filtrate pump.

11. A method for administering a blood treatment therapy comprising
    providing (a) a substitution fluid pump, (b) a filtrate pump, and (c) a controller for managing fluid flow of a treatment using the substitution fluid pump and the filtrate pump;
    inputting into the controller an actual substitution fluid input, an actual filtration input, a prescribed substitution fluid input, and a prescribed filtration input;
    comparing a difference of the actual substitution fluid input and the actual filtration input with each of the prescribed substitution fluid input and the prescribed filtration input to produce a flow rate error signal;
    calculating a total fluid loss value based at least upon the flow rate error signal;
    determining whether the total fluid loss value is: (a) below a predetermined lower threshold; (b) above a predetermined upper threshold; or (c) between the predetermined lower threshold and the predetermined upper threshold;
    controlling a rate of the filtrate pump based at least in part upon the prescribed filtration input, the flow rate error signal, and the total fluid loss;
    controlling a rate of the substitution pump based at least in part upon the prescribed substitution fluid input, the flow rate error signal, and the total fluid loss value; and
    outputting from the controller an alarm signal if the total fluid loss value is below the predetermined lower threshold or above the predetermined upper threshold.

12. The method of claim 11, further comprising storing a value representing the calculated total fluid loss.

13. The method of claim 11, further comprising stopping the therapy if the total fluid loss value is either below the predetermined lower threshold or above the predetermined upper threshold.

14. The method of claim 11, further comprising calculating a desired filtration input based on the prescribed filtration input and the prescribed substitution fluid input.

15. The method of claim 11, further comprising
    if the total fluid loss value is above the predetermined upper threshold, activating the filtrate pump without activating the substitution pump until a desired balance of total fluid loss is attained.

16. The method of claim 11 further comprising
    if the total fluid loss value is below the predetermined lower threshold, activating the substitution pump without activating the filtrate pump until a desired balance of total fluid loss is attained.

* * * * *

UNITED STATES PATENT AND TRADEMARK OFFICE
CERTIFICATE OF CORRECTION

| | | |
|---|---|---|
| PATENT NO. | : 8,246,566 B2 | Page 1 of 1 |
| APPLICATION NO. | : 11/960529 | |
| DATED | : August 21, 2012 | |
| INVENTOR(S) | : Lannoy | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 581 days.

Signed and Sealed this
Seventeenth Day of March, 2020

Andrei Iancu
*Director of the United States Patent and Trademark Office*